United States Patent [19]

Hsu et al.

[11] Patent Number: 4,652,344
[45] Date of Patent: Mar. 24, 1987

[54] PREPARATION OF 1,1-DIMETHOXYCYCLOHEXANE

[75] Inventors: Chao-Yang Hsu, Media; Paul E. Ellis, Jr., Downingtown, both of Pa.

[73] Assignee: Sun Refining and Marketing Company, Philadelphia, Pa.

[21] Appl. No.: 803,198

[22] Filed: Dec. 2, 1985

Related U.S. Application Data

[63] Continuation-in-part of Ser. No. 621,813, Jun. 18, 1984, abandoned.

[51] Int. Cl.$^4$ .......................... C07C 41/58; B01D 3/36
[52] U.S. Cl. ......................................... 203/96; 203/79; 568/591
[58] Field of Search .................................... 203/92–97, 203/54, 62, 17, 79; 568/591, 592, 594

[56] References Cited

U.S. PATENT DOCUMENTS

| 2,762,760 | 9/1956 | Walker | 203/96 |
| 2,822,402 | 2/1958 | McCoy | 568/591 |
| 2,845,384 | 7/1958 | Williston | 203/68 |

FOREIGN PATENT DOCUMENTS

| 651644 | 11/1962 | Canada | 568/591 |
| 82465 | 6/1971 | German Democratic Rep. | 203/96 |
| 50-111047 | 9/1975 | Japan | 568/591 |

OTHER PUBLICATIONS

Taylor et al., *Synthesis*, 467, 1977.
Helferich et al.: *Ber.*, 57B, 795, (1924).
McCoy et al.: *J. Org. Chem.*, 22, p. 1175, (1957).

*Primary Examiner*—Wilbur Bascomb
*Attorney, Agent, or Firm*—J. Edward Hess; Donald R. Johnson; Stanford M. Back

[57] ABSTRACT

Dimethoxycyclohexane, prepared by reacting cyclohexanone with methanol, may be recovered from the product mixture in substantially pure form by first adding water as an azeotropic agent to said mixture to form an azeotrope with unreacted cyclohexanone, removing said azeotrope by distillation, thereby leaving substantially pure dimethoxycyclohexane.

2 Claims, No Drawings

PREPARATION OF 1,1-DIMETHOXYCYCLOHEXANE

CROSS-REFERENCE TO RELATED CASES

This application is a continuation-in-part of Ser. No. 621,813, filed June 18, 1984 and now abandoned.

BACKGROUND OF THE INVENTION

1. Scope of the Invention

This invention relates to a process for the production of dimethoxycyclohexane. More particularly, it relates to an improved process for reaction of methanol with cyclohexanone in the presence of an acidic catalyst to form dimethoxycyclohexane ("DMC") in good yield and under conditions which facilitate the recovery of the product from the reaction mixture. As described in detail below, this is achieved by carrying out the reaction in the presence of a strongly acidic catalyst, and thereafter adding water as an azeotropic agent to separate unreacted cyclohexanone from the product by distillation, thereby recovering substantially pure DMC, and thus achieve significant economies over the prior art processes described below.

2. Description of the Prior Art 1,1-Dimethoxycyclohexane is an acetal which is a valuable intermediate in the production of perfumes and agricultural chemicals and which can be useful as dehydrating agent. Laboratory methods for the preparation of 1,1-dimethoxycyclohexane are unsatisfactory for commercial processes because they utilize expensive starting materials such as trimethylorthoformate [E. Taylor and C. Chiang, *Synthesis*, 467 (1977)] or methyl orthosilicate [B. Helferich and J. Hausen, *Ber.*, 57B, 795 (1924)].

1,1-Dimethoxycyclohexane can be produced by the simple equilibrium controlled reaction of cyclohexanone with methanol under acidic conditions as follows:

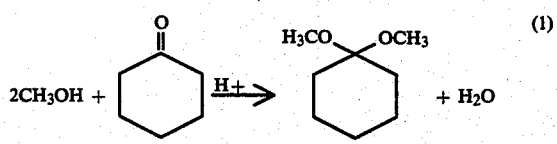

McCoy et. al. [*J. Org. Chem.*, 22,1175 (1957); U.S. Pat. No. 2,822,402, Feb. 4, 1958] used methanolic HCl as the catalyst to produce 1,1-dimethoxycyclohexane. Their method suffers from low conversion of cyclohexanone and subsequent difficulty in separating the cyclohexanone from the product because of similar boiling points. Arashi et. al. [*Jpn. Kokai* 75, 111, 047, Sept. 1, 1975] improve the process by distilling with added hydrazine to facilitate the separation of cyclohexanone from 1,1-dimethoxycyclohexane. They also use drying agents to improve the conversion of cyclohexanone.

Canadian Pat. No. 651,644, while teaching the production of dimethoxycyclohexane, recovers this product, in part, by extracting unreacted cyclohexanone with large volumes of water, which is an inefficient method. Walker, U.S. Pat. No. 2,762,760, while teaching the formation of a known cyclohexanone/water azeotrope, does so in a process involving no ketals whatever and does not suggest or teach the advantages of using such an azeotrope in the preparation and purification of DMC.

SUMMARY OF THE INVENTION

In accordance with this invention, there is provided a process for making and recovering highly pure 1,1-dimethoxycyclohexane by reacting cyclohexanone and methanol in the presence of a strongly acidic catalyst, preferably a strongly acidic ion-exchange resin, to form a reaction product comprising 1,1-dimethoxycyclohexane, unreacted cyclohexanone and methanol, and minor amounts of water, adding additional water to the reaction product in amounts sufficient to form an azeotrope with the unreacted cyclohexanone, distilling the resulting mixture to first remove methanol and then the azeotrope of water and cyclohexanone, and recovering substantially pure 1,1-dimethoxycyclohexane.

DESCRIPTION OF THE PROCESS

In carrying out this process a solution of cyclohexanone in methanol is desirably passed over a strongly acidic ion-exchange resin at about 0°–25° C. and at atmospheric pressure. The molar ratio of methanol to cyclohexanone employed is desirably about 2–20:1, and preferably about 10–15:1, i.e. a significant excess of methanol is preferred. The resulting mixture of unreacted methanol and cyclohexanone, and the desired product, 1,1-dimethoxycyclohexane, and water, is then subjected to distillation. Before distillation, the amount of cyclohexanone present is measured by gas chromatography and an additional amount of water is added sufficient to give an azeotropic composition of cyclohexanone and water, with the water comprising generally up to about 55 wt. % based on the amount of cyclohexanone. When the amount of water is reduced significantly below about 55 wt. %, little if any azeotrope forms, while amounts substantially in excess of 55 wt. % result in hydrolysis of the product. Therefore, amounts of water in the range of about 50–60 wt. % are desired, with amounts of about 53–57 wt. % being preferred. After first removing unreacted methanol (e.g. by distillation at temperatures of about 65° C.), the cyclohexanone/water azeotrope is removed by distillation, desirably at atmospheric pressure, and generally at temperatures of about 90°–95° C. The 1,1-dimethoxycyclohexane product may then be recovered by distillation, preferably at reduced pressures.

When an ion-exchange resin column is employed, it can be run anywhere from about 0° C. to ambient temperature, with the lower temperature giving a higher yield of 1,1-dimethoxycyclohexane. Strongly acidic ion-exchange resins such as Amberlyst-15 and Amberlyst XN 1010 (from the Rohm and Haas Co.) and Dowex 50 (from the Dow Co.) are acceptable, with Amberlyst XN 1010 being preferred. Each of these resins is of the general class of resins having the composition comprising a sulfonic acid-functionalized polystyrene-divinylbenzene copolymer. At the bottom of the column, a small amount of strong base ion-exchange resin such as Amberlyst A-27 may be included (Rohm and Haas Co.) to remove any acid from the reaction product. A small amount of a weak base such as sodium methoxide or sodium bicarbonate can also be added to the distillation flask to prevent the back reaction of the acetal with water. The process can be run continuously by conventional means or batchwise as described in Example 1 below.

The process of this invention will now be illustrated by, but is not intended to be limited to, the following example.

EXAMPLE I

This example will illustrate the production of 1,1-dimethoxycyclohexane using the process of this invention.

A 1 in. diameter jacketed column was filled with 37 g. of Amberlyst XN 1010 to a height equal to 10 cm. on top of 2 cm. of Amberlyst A-27. The column was operated at atmospheric pressure and 0°-1° C. The feed used was a molar ration of 13:1 of methanol to cyclohexanone at a feed rate of 0.5-1.0 ml./min. At this flow rate and temperature, the conversion of cyclohexanone was 73-74%. Approximately, 600 ml. of solution was removed from the column at 1° C. and was analyzed by gas chromatography showing 131.1 ml. of the desired 1,1-dimethoxycyclohexane, 32.7 ml. of cyclohexanone, 417 ml. of methanol and 15.5 ml. of water. To this was added 23 ml. of water to give 55 wt. % water azeotrope of water/cyclohexanone. This material was distilled using a 5 tray column at atmospheric pressure. At 64°-65° C., the methanol was removed. From 88°-96° C. the azeotrope cyclohexanone and water was removed together with small amounts of the product. Using 50 mm. Hg. reduced pressure, 93 ml. of substantially pure 1,1-dimethoxycyclohexane was then removed between 68°-73° C.

What we claim is:

1. In the process for the production of dimethoxycyclohexane by the reaction of methanol with cyclohexanone in the presence of an acidic catalyst, the improvement comprising adding water to the resulting reaction product mixture in amounts sufficient to form an azeotrope with any unreacted cyclohexanone, removing said azeotrope by distillation, and thereafter recovering substantially pure dimethoxycyclohexane from the reaction mixture, wherein the water is added in amounts sufficient to provide about 50-60 wt. % water based on the amount of unreacted cyclohexanone present.

2. The process of claim 1 wherein the water is added in amounts sufficient to provide about 55 wt. % water based on the amount of unreacted cyclohexanone present.

* * * * *